(12) United States Patent
Kim et al.

(10) Patent No.: US 8,932,864 B2
(45) Date of Patent: Jan. 13, 2015

(54) METHOD OF IDENTIFYING GLYCATED PROTEIN IN SAMPLE AND DEVICE FOR THE GLYCATED PROTEIN

(71) Applicant: Samsung Electronics Co., Ltd., Suwon-si (KR)

(72) Inventors: Sang-kyu Kim, Yongin-si (KR); Sung-ha Park, Incheon (KR); Kyung-mi Song, Suwon-si (KR); Soo-suk Lee, Suwon-si (KR); Youn-suk Choi, Yongin-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 1 day.

(21) Appl. No.: 13/846,495

(22) Filed: Mar. 18, 2013

(65) Prior Publication Data

US 2014/0065714 A1    Mar. 6, 2014

(30) Foreign Application Priority Data

Sep. 6, 2012   (KR) .................. 10-2012-0098856

(51) Int. Cl.
*G01N 33/72*   (2006.01)
*G01N 33/68*   (2006.01)
*G01N 33/48*   (2006.01)

(52) U.S. Cl.
CPC .................................... *G01N 33/723* (2013.01)

USPC ............... 436/67; 436/63; 436/66; 436/87; 436/164; 436/174; 436/175; 436/177; 436/178; 422/82.09; 422/534; 422/535

(58) Field of Classification Search
USPC ........... 436/63, 66, 67, 86, 87, 164, 174, 175, 436/177, 178; 422/82.05, 82.09, 527, 533, 422/534, 535

See application file for complete search history.

(56) References Cited

U.S. PATENT DOCUMENTS

| | | | |
|---|---|---|---|
| 5,242,842 A * | 9/1993 | Sundrehagen | 436/536 |
| 5,686,316 A * | 11/1997 | Fiechtner et al. | 436/518 |
| 5,877,025 A | 3/1999 | Edwards et al. | |
| 6,162,645 A * | 12/2000 | Lee et al. | 436/67 |
| 6,300,142 B1 * | 10/2001 | Andrewes et al. | 436/518 |
| 6,399,293 B1 | 6/2002 | Pachl et al. | |
| 6,562,581 B2 * | 5/2003 | Law et al. | 435/14 |
| 7,374,943 B2 | 5/2008 | Holtlund et al. | |
| 7,695,973 B2 | 4/2010 | McCroskey et al. | |
| 2004/0089616 A1 * | 5/2004 | Kellogg et al. | 210/749 |
| 2009/0093012 A1 * | 4/2009 | Bae et al. | 435/29 |
| 2011/0143364 A1 * | 6/2011 | Kim et al. | 435/7.1 |
| 2012/0088253 A1 * | 4/2012 | Bae et al. | 435/7.25 |

FOREIGN PATENT DOCUMENTS

KR   1020100137851 A   12/2010
KR   1020110002293 A   1/2011

* cited by examiner

*Primary Examiner* — Maureen Wallenhorst
(74) *Attorney, Agent, or Firm* — Leydig, Voit & Mayer, Ltd.

(57) ABSTRACT

Provided is a method and device for identifying glycated protein in a sample using a matrix including a boronic acid moiety that binds glycated proteins.

11 Claims, 4 Drawing Sheets

METHOD OF IDENTIFYING GLYCATED PROTEIN IN SAMPLE AND DEVICE FOR THE GLYCATED PROTEIN

CROSS-REFERENCE TO RELATED APPLICATION

This application claims the benefit of Korean Patent Application No. 10-2012-0098856, filed on Sep. 6, 2012 in the Korean Intellectual Property Office, the disclosure of which is incorporated herein in its entirety by reference.

BACKGROUND

1. Field

The present disclosure relates to methods of identifying a glycated protein in a sample and devices for the glycated protein

2. Description of the Related Art

Glycated hemoglobin is hemoglobin bound with saccharides. Hemoglobin may have saccharides bound to A chains. For example, glycated hemoglobin may include A1a, A1b, A1c, or a combination thereof. In A1a, A1b and A1c, approximately 60% to 80% of hemoglobin are found to be hemoglobin A1c (HbA1c) in which glucose is bound to a valine site at an N-terminal of the β-chain.

Glycated hemoglobin is indicative of the average blood sugar (plasma glucose) concentration during the last 2 to 3 months of a patient, and thus, glycated hemoglobin may become a good index to indicate a blood sugar level of a body. In a method of measuring blood sugar to measure glucose of the related art, the blood sugar levels have different values depending on whether the measurement is performed in an empty stomach or after meal, but the measurement method based on glycated hemoglobin may not be affected by short-term variations such as a measurement before or after having meals.

SUMMARY

Provided are methods of efficiently identifying glycated protein in a sample. In one embodiment, the method comprises incubating a matrix to which a compound containing a boronic acid moiety is fixed with a sample including glycated protein and non-glycated protein to provide a reaction mixture comprising a matrix bound with glycated protein; removing the matrix bound with glycated protein from the reaction mixture; measuring a signal from the non-glycated protein in the reaction mixture; and comparing the measured signal of the non-glycated protein in the reaction mixture with a signal measured from a sample including glycated protein and non-glycated protein.

Provided are devices for efficiently identifying glycated protein. In one embodiment, the device comprises a first region including comprising a first reaction chamber, a separation unit for separating a matrix bound with glycated protein from a reaction mixture, wherein the separation unit is in fluid communication with the first reaction chamber, and first detecting region in fluid communication with the separation unit; and a second region including a second reaction chamber, and a second detecting region in fluid communication with the second reaction chamber.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
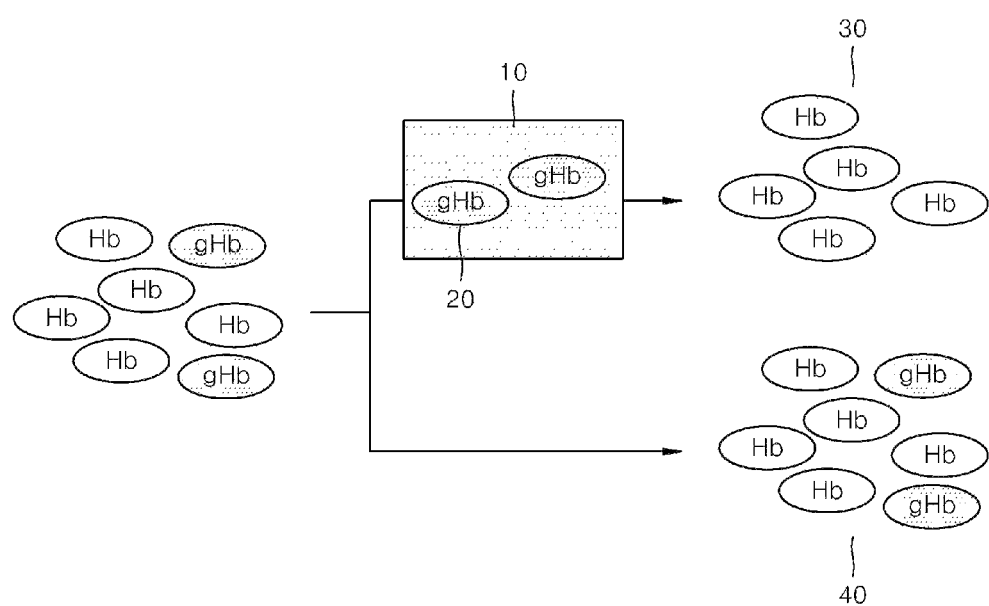
FIG. 1 illustrates a method of identifying glycated protein in a sample, according to an embodiment. gHb and Hb refer to glycated hemoglobin and non-glycated hemoglobin, respectively.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

According to an aspect of the present invention, a method of identifying glycated protein in a sample includes: incubating (a) a matrix to which a compound containing a boronic acid moiety is fixed with (b) a sample including glycated protein to provide a reaction mixture comprising a matrix bound with glycated protein; removing the matrix bound with glycated protein from the reaction mixture; measuring a signal from non-glycated protein in the reaction mixture; and comparing the measured signal of the non-glycated protein in the reaction mixture with a signal measured from the sample including glycated protein and non-glycated protein.

The method includes incubating (a) a matrix to which a compound including a boronic acid moiety is fixed with (b) a sample including glycated protein to provide a reaction mixture comprising a matrix bound with glycated protein.

"Boronic acid moiety" means a moiety with $(OH)_2B-$. A compound including the boronic acid moiety may be $(OH)_2B-$ or $(OH)_2B-R_1-$, wherein $R_1$ is a hydrocarbon with a carbon number of about 1 to about 30. $R_1$ may be, for example, a saturated or unsaturated hydrocarbon which is straight-chained or branched with a carbon number of about 1 to about 30. $R_1$ may, for example, include an aromatic hydrocarbon with a carbon number of about 1 to about 30. $R_1$ may be methylene, ethylene, propylene, butylene, iso-butylene, pentylene, or phenylene. The boronic acid moiety may or may not include dye. The dye may not include fluorescent dye, phosphorescent dye, or a combination thereof. The dye may emit a detectable signal which distinguishes itself from a signal of non-glycated protein. For example, the dye may be a dye with an azo group.

"Glycated protein" may include a glycated polypeptide or a glycated amino acid. "Glycated protein" may be, for example, glycated hemoglobin, a fragment of the glycated hemoglobin, a glycated amino acid, or a combination thereof. The glycated hemoglobin includes A1a, A1b, A1c, or a combination thereof.

A matrix with a compound including the boronic acid moiety fixed thereto may be a solid particle. The particle may have a cross section length (e.g., diameter) of about 10 nm to about 1,000 μm. The particle may have a particle size of, for example, about 100 nm to about 1,000 μm, about 1 μm to about 500 μm, about 1 μm to about 300 μm, about 1 μm to about 100 μm, about 1 μm to about 80 μm, about 1 μm to about 60 μm, about 1 μm to about 50 μm, about 1 μm to about 30 μm, about 1 μm to about 20 μm, about 1 μm to about 10 μm, about 10 μm to about 1,000 μm, about 10 μm to about 500 μm, about 10 μm to about 400 μm, about 10 μm to about 300 μm, about 10 μm to about 200 μm, about 10 μm to about 100 μm, about 10 μm to about 80 μm, about 10 μm to about 60 μm, about 10 μm to about 50 μm, about 10 μm to about 30 μm, about 10 μm to about 20 μm, about 50 μm to about 1,000 μm, about 50 μm to about 500 μm, about 50 μm to about 300 μm, about 50 μm to about 100 μm, about 50 μm to about 80 μm, about 50 μm to about 60 μm, about 100 μm to about 1,000 μm, about 100 μm to about 500 μm, about 100 μm to about 400 μm, about 100 μm to about 300 μm, or about 100 μm to about 200 μm.

When the matrix, for example, the particle, has the shape of a sphere, the length of the cross section indicates a diameter. A matrix to which a compound including the boronic acid moiety is fixed may have a shape of a sphere, a polygon, a membrane, a plate, or a combination thereof.

The particle may be a metal particle. The particle may include gold, silver, aluminum, silicon, copper, iron, silica, agarose, cellulose, plastic material, or a combination thereof. The particle may be a magnetic particle.

The membrane may be a porous membrane. The porous membrane may have such a pore size that glycated protein or non-glycated protein may permeate through the membrane, but a matrix with a compound including the boronic acid moiety fixed thereto or a complex of glycated protein and a matrix with a compound including the boronic acid moiety fixed thereto may not permeate through the membrane.

Glycated protein, for example, a sample including glycated hemoglobin, may include any protein as long as glycated protein is included. For example, the glycated protein may be blood with glycated hemoglobin or blood lysate. Also, the sample may include cells, tissue, or a combination thereof.

The incubation may be performed under a condition enabling a covalent bond between the boronic acid and cis-diol of saccharides to be triggered. For example, incubation may be performed with or without stirring at room temperature.

The method includes removing the matrix bound with glycated protein from the reaction mixture. The removing may be performed by centrifugation, filtration, precipitation, or a combination thereof. Consequently, the non-glycated protein with removed glycated protein-matrix complex, for example, non-glycated hemoglobin, may be obtained.

The method includes measuring a signal from the non-glycated protein in the reaction mixture. The measuring of a signal may include measuring an optical signal, an electrical signal, a mechanical signal, or a combination thereof. The measuring a signal may include measuring an optical signal specific to glycated hemoglobin itself. For example, when the glycated protein is glycated hemoglobin, the measuring of a signal may include measuring an optical signal specific to non-glycated hemoglobin. For example, the measuring a signal may include measuring light absorbance specific to glycated or non-glycated hemoglobin, for example, light absorbance at about 400 nm to about 430 nm.

The method includes comparing the measured signal of the non-glycated protein in the reaction mixture with a signal measured from a sample including glycated protein and non-glycated protein. The measuring of a signal may include measuring an optical signal, an electrical signal, a mechanical signal, or a combination thereof. The measuring of a signal may include measuring an optical signal specific to the glycated protein itself, non-glycated protein, or a combination thereof. For example, when the glycated protein is glycated hemoglobin, the measuring of a signal may include measuring an optical signal specific to glycated protein and non-glycated hemoglobin. For example, the measuring of a signal may include measuring light absorbance specific to hemoglobin, for example, light absorbance at about 400 nm to about 430 nm. That is, the measuring of a signal may include measuring the signal of total hemoglobin.

In comparing operation of the measured signal, a sample including glycated protein and non-glycated protein is a reaction product obtained by incubating the matrix to which a compound including the boronic acid moiety is fixed with a sample including glycated protein to provide a reaction mixture comprising a matrix bound with glycated protein, followed by incubating the matrix bound with glycated protein in the presence of a material having a higher affinity to the boronic acid than glycated protein. The material having a higher affinity to the boronic acid than the glycated protein includes, but is not limited to, sorbitol, mannitol, adonitol, erythritol, and a combination thereof.

An operation of measuring a signal from non-glycated protein in the reaction mixture; and an operation of measuring a signal from a sample including glycated protein and non-glycated protein may be performed simultaneously or sequentially. Also, an operation of measuring a signal from non-glycated protein in the reaction mixture; and an operation of measuring a signal from a sample including glycated protein and non-glycated protein may be performed by the same device. The device may be a device for identifying glycated protein.

FIG. 1 illustrates a method of identifying glycated protein in a sample, according to an embodiment. As shown in FIG. 1, only glycated hemoglobin (gHb) may be selectively removed by bringing glycated hemoglobin (gHb) and non-glycated hemoglobin (Hb) into contact with the boronic acid-conjugated matrix. As a result, a signal (OD1) measured from non-glycated hemoglobin (Hb) 30 may be obtained from a signal (OD2) measured from a mixture of glycated hemoglobin (gHb) and non-glycated hemoglobin (Hb) 40, and a concentration of glycated hemoglobin within the sample may be identified from OD2 and OD1.

According to another embodiment of the present invention, a device for identifying glycated protein includes: a first region including a first reaction chamber, a separation unit for separating a matrix bound with glycated protein that is in fluid communication with the first reaction chamber and a first detecting region in fluid communication with the separation unit; and a second region including a second reaction chamber and a second detecting region in fluid communication with the second reaction chamber. The fluid passage between the first reacting chamber and the first detecting region may be provided by a matrix labeled with the boronic acid (e.g., a passage comprising the matrix).

A matrix bound with glycated protein may have a particle size of, for example, about 10 nm to about 1,000 μm in cross section length. The particle may be, for example, about 100 nm to about 1,000 μm, about 1 μm to about 500 μm, about 1 μm to about 300 μm, about 1 μm to about 100 μm, about 1 μm to about 80 μm, about 1 μm to about 60 μm, about 1 μm to about 50 μm, about 1 μm to about 30 μm, about 1 μm to about 20 μm, about 1 μm to about 10 μm, about 10 μm to about 1,000 μm, about 10 μm to about 500 μm, about 10 μm to about 400 μm, about 10 μm to about 300 μm, about 10 μm to about 200 μm, about 10 μm to about 100 μm, about 10 μm to about 80 μm, about 10 μm to about 60 μm, about 10 μm to about 50 μm, about 10 μm to about 30 μm, about 10 μm to about 20 μm, about 50 µm to about 1,000 µm, about 50 µm to about 500 µm, about 50 µm to about 300 µm, about 50 µm to about 100 µm, about 50 µm to about 80 µm, about 50 µm to about 60 µm, about 100 µm to about 1,000 µm, about 100 µm to about 500 µm, about 100 µm to about 400 µm, about 100 µm to about 300 µm, or about 100 µm to about 200 µm.

When the particle has a spherical shape, the length of the cross section becomes a diameter. A particle bound with glycated protein may have a shape of a sphere, a polygon, a membrane, a plate, or a combination thereof.

The membrane may be a porous membrane. The porous membrane may have such a pore size that glycated protein or non-glycated protein may permeate through the membrane, but a matrix with a compound including a boronic acid moiety fixed thereto may not permeate through the membrane.

The particle may be a metal particle. The particle may be a magnetic particle. The particle may include gold, silver, aluminum, silicon, copper, iron, silica, agarose, cellulose, plastic material, or a combination thereof. The particle may be a magnetic particle.

The separation unit for separating a matrix bound with glycated protein may be a unit for separating the matrix from glycated protein, protein, or a combination thereof. For example, the separation unit may be a centrifuge device, a filtering device or a combination thereof. The filtering device may be a porous membrane that a matrix bound with glycated protein, for example, glycated hemoglobin, may not penetrate therethrough.

The first detecting region may have the shape of a channel or chamber. The first detecting region may be optically transparent. In the first detecting region, a signal measuring unit to measure a signal from glycated proteins existing in this region may be disposed. For example, a measuring device of measuring optical signals, electrical signals, or a combination thereof may be disposed.

The first chamber may be in fluid communication with a chamber for storing a matrix bound with glycated protein. Also, the first chamber may be connected to an inlet.

The second region may or may not include a separation unit for separating a matrix bound with glycated protein.

The device may be a microfluidic device having an inlet and outlet which are connected via a channel or a chamber. The microfluidic device may have one or more channels or chambers with about 10 nm to about 1,000 µm in cross section length. When the cross section is a spherical shape, the length becomes a diameter.

Figure 2:
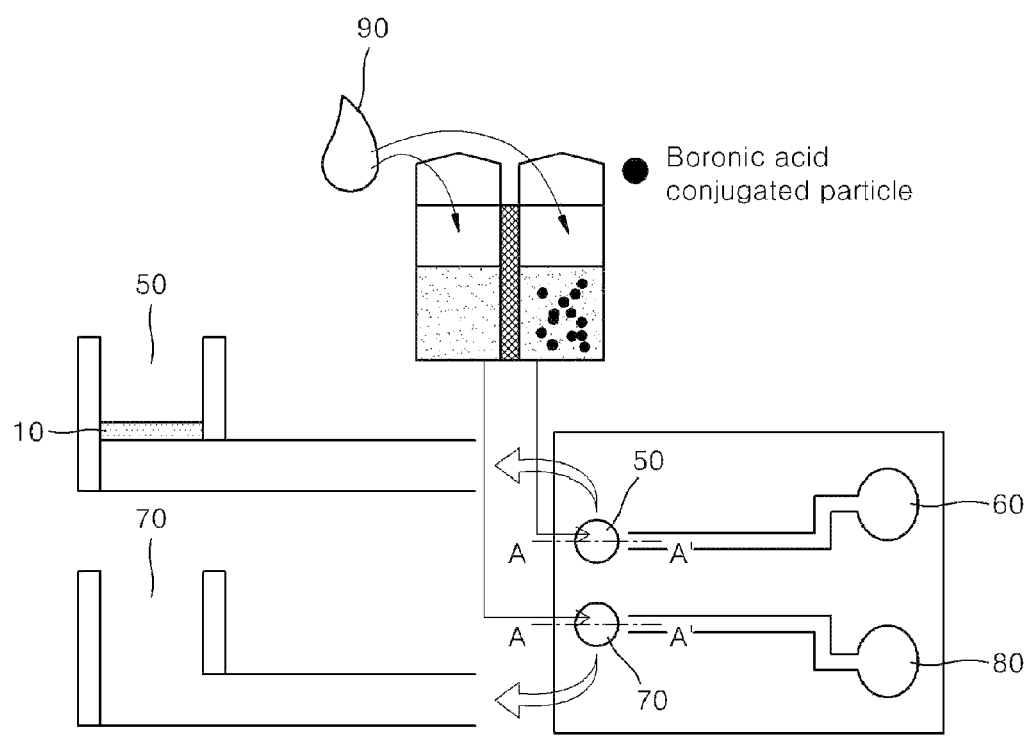
FIG. 2 illustrates a method of identifying glycated protein in a sample and a device used therefor.

FIG. 2 illustrates a method of identifying glycated protein in a sample and a device used therefor, according to an embodiment. Upper left and lower left drawings in FIG. 2 illustrate sectional views of the first region and the second region, respectively, which are taken along A-A', respectively.

As illustrated in FIG. 2, a first reaction chamber 50 includes a porous membrane that allows the boronic acid conjugated matrix not to permeate therethrough but allows glycated hemoglobin, non-glycated hemoglobin, or combinations thereof to permeate therethrough. A second reaction chamber 70 does not include a porous membrane.

First, a whole blood sample 90 was incubated in lysis buffer without a matrix or a boronic acid-conjugated matrix, added to the first reaction chamber 50 and the second reaction chamber 70, and then moved to first and second detecting regions by applying a pressure. An optical measuring device is disposed in the first and second detecting regions to measure optical signals for the solution included in the region. The device may further include a lysis buffer chamber for storing lysis buffer, and/or a chamber of boronic acid-conjugated matrix to store boronic acid-conjugated matrix, wherein the lysis buffer chamber is in fluid communication with the first reaction chamber 50 and/or the second reaction chamber 70.

Figure 3:
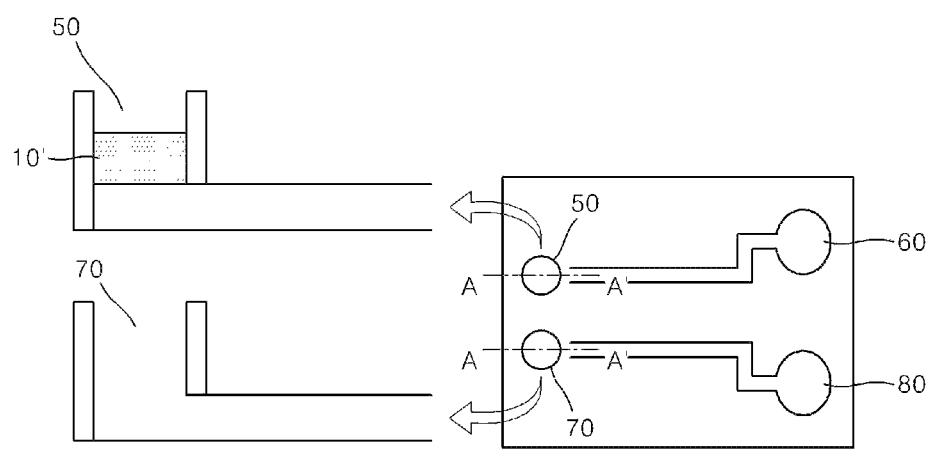
FIG. 3 illustrates a method of identifying glycated protein in a sample and a device used therefor.

FIG. 3 illustrates a method of identifying glycated protein in a sample and a device used therefor, according to an embodiment. The device illustrated in FIG. 3 is identical to the device of FIG. 2, except that the boronic acid-conjugated matrix 10' is fixed to a separation unit such as a membrane or a glass fiber filter.

Figure 4:
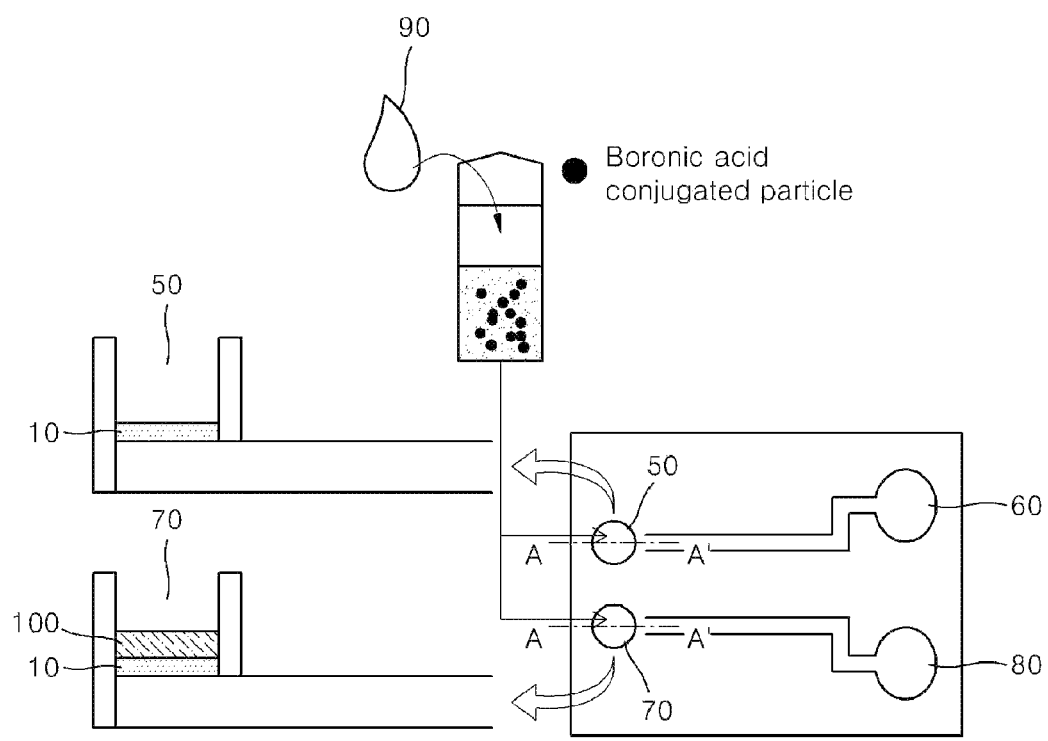
FIG. 4 illustrates a method of identifying glycated protein in a sample and a device used therefor.

FIG. 4 illustrates a method of identifying glycated protein in a sample and a device used therefor, according to an embodiment. The device illustrated in FIG. 4 is identical to the device of FIG. 2, except that a material binding to the boronic acid with higher affinity than glycated hemoglobin, for example, sorbitol, is fixed to the second reaction chamber and a porous membrane is further included thereunder. This method is the same as the method of FIG. 2, except that a reaction product of hemolysed whole blood and the boronic acid-conjugated matrix are added to the second reaction chamber.

The following non-limiting examples serve to further illustrate the methods, compositions, and devices described herein.

EXAMPLE 1

Identification of Glycated Hemoglobin Using an Agarose Matrix that Includes a Boronic Acid Moiety Samples of whole blood were prepared. 10 µL of each of the whole blood samples was mixed with 200 µL of a solution in which hemolysis buffer (250 mM ammonium acetate, 40 mM $MgCl_2$, 0.06% SDS, and 0.07% Triton X 100) and agarose particles having an average diameter of about 100 µm bound with a boronic acid (aminophenylboronate agarose P6XL, Prometic). Mixing by pipetting was performed for a minute. Afterwards, the resultant mixture was put into a sample inlet and filtered under pressure through a polycarbonate membrane having pores of about 0.8 µm diameter. This allowed the agarose particles bound with the boronic acid to be left and other materials to permeate through the membrane. The light absorbance of a filtrate was measured at about 405 nm. Hereinafter, the measured light absorbance will be referred to as OD1. The reaction was carried out by reacting the lysate and the boronic acid-conjugated agarose particles in a first reaction chamber, filtering the reactants through the membrane, and then measuring the light absorbance in a first detecting region.

To measure the total quantity of hemoglobin, 10 µL of each of the whole blood samples was mixed with 200 µL of hemolysis buffer, and pipetting was performed for a minute. The lysate was put into the sample inlet, and then pressured to be transported to a second detecting region in fluid communication with a second reaction chamber. The light absorbance of the transported reaction mixture was measured at about 405 nm. Hereinafter, the measured light absorbance will be referred to as OD2. The lysate was transferred from the second reaction chamber to the second detecting region, and the light absorbance was measured in the second detecting region.

The capture ratio representing a ratio of glycated hemoglobin fixed to particles was calculated by (OD2−OD1)/OD2. The correlation between the capture ratio and HbA1c (%) was y=0.0098x+0.1155 (y is a capture ratio and x is HbA1c (%)), and the correlation coefficient $R^2$ was 0.9823.

EXAMPLE 2

Identification of Glycated Hemoglobin Using Silica Particles that Include a Boronic Acid Moiety 10 µL of each of the blood samples having different concentrations of glycated hemoglobin was hemolysed by being dispersed in 250 µL of hemolysis buffer (250 mM ammonium acetate, 40 mM $MgCl_2$, 0.06% SDS, and 0.07% Triton X 100). 80 µL of the acquired lysate and 20 µL of a solution containing boronic acid-conjugated silica particles with an average diameter of about 50 µm (5 mg particles) were mixed together, and pipetting was performed for about 5 minutes.

30 µL of the mixture was filtered through a polycarbonate membrane with pores of about 0.8 µm diameter to allow the boronic acid-conjugated silica particles to be left and other materials to permeate through the membrane. The light absorbance of the filtrate was measured at 405 nm, which is a wavelength specifically absorbed by the heme structure of hemoglobin. Hereinafter, the measured light absorbance will be referred to as OD1. The reaction was performed by reacting the lysate and the boronic acid-conjugated silica particles in the first reaction chamber, filtering the product through the membrane, and measuring the light absorbance in the first detecting region.

To measure the total quantity of hemoglobin, 80 µL of lysate obtained in the same manner as described above was mixed with 20 µL of hemolysis buffer, and pipetting was performed for about 5 minutes. Next, the mixture was transported to the second detecting region in fluid communication with the second reaction chamber. The light absorbance of the transported reaction mixture was measured at about 405 nm. Hereinafter, the measured light absorbance will be referred to as OD2. The lysate was transferred from the second reaction chamber to the second detecting region without membrane filtration and the light absorbance was then measured in the second detecting region.

The capture ratio representing a ratio of glycated hemoglobin fixed to particles was calculated by (OD2−OD1)/OD2. The correlation between the capture ratio and HbA1c (%) was y=0.0093x+0.1891 (y is a capture ratio and x is HbA1c (%)), and the correlation coefficient $R^2$ was 0.9924.

EXAMPLE 3

Identification of Glycated Hemoglobin Using Silica Particles that Include a Dried Boronic Acid Moiety 10 µL of each of the blood samples having different concentrations of glycated hemoglobin (HbA1c)(%) was hemolysed by being dispersed in 250 µL of hemolysis buffer (250 mM ammonium acetate, 40 mM $MgCl_2$, 0.06% SDS, and 0.07% Triton X 100). 30 µL of the acquired lysate was added to the first reaction chamber where 2.5 mg of boronic acid-conjugated silica particles in average diameter about 50 µm were dried and incubated at 37° C. for about 3 minutes.

For the first region, 30 µL of the mixture was filtered through a polycarbonate membrane with pores of about 0.8 µm diameter to allow the boronic acid-conjugated silica particles to be left and other materials to permeate through the membrane. The light absorbance of the filtrate was measured at about 405 nm. Hereinafter, the measured light absorbance will be referred to as OD1. The reaction was performed by reacting the lysate and the boronic acid-conjugated silica particles in the first reaction chamber, filtering the product through the membrane, and measuring the light absorbance in the first detecting region.

To measure the total quantity of hemoglobin, for the second region, 30 µL of the mixture was transported to the second detecting region in fluid communication with the second reaction chamber without membrane filtration. The light absorbance of the transported reaction mixture was measured at about 405 nm. Hereinafter, the measured light absorbance will be referred to as OD2.

The capture ratio representing a ratio of glycated hemoglobin fixed to particles was calculated by (OD2−OD1)/OD2. The correlation between the capture ratio and HbA1c (%) was y=0.0017x+0.324 (y is a capture ratio and x is HbA1c(%)), and the correlation coefficient $R^2$ was 1.0.

In a method according to one embodiment, glycated protein in a sample may be efficiently identified without any interference among samples. Also, glycated protein in a sample may be efficiently identified without a washing process.

In a method of identifying glycated protein in a sample according to another embodiment, glycated protein in a sample may be efficiently identified.

In a device for identifying glycated protein according to another embodiment, the device may be used for efficiently identifying glycated protein in a sample.

The invention according to one or more embodiments uses optical characteristics unique of hemoglobin unlike the methods of the related art using optical characteristics of chromogen or fluorescent materials. However, according to the circumstances, coloring may be measured by drying a chromogen, which develops color by reacting with hemoglobin, onto a measuring part. A measuring system may be realized even with a simple fluid manipulation without a need of washing chromogens or fluorescent materials that are not involved in a reaction, and thus, the system is suitable for small-sized devices such as point-of-care test devices.

It should be understood that the exemplary embodiments described therein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A device for identifying glycated protein comprising:
   (a) a first region comprising
      (i) a first reaction chamber,
      (ii) a separation unit for separating a matrix bound with glycated protein from a reaction mixture, wherein the separation unit is in fluid communication with the first reaction chamber, and
      iii) a first detecting region in fluid communication with the separation unit, wherein the separation unit is a porous membrane to which a compound comprising a boronic acid moiety is fixed, and wherein the separation unit defines the first reaction chamber and a passage fluidly connecting the first reaction chamber and the first detecting region; and
   (b) a second region including
      (i) a second reaction chamber, and
      (ii) a second detecting region in fluid communication with the second reaction chamber, wherein the second detecting region does not include a separation unit for separating a matrix bound with glycated protein from a reaction mixture.

2. The device of claim 1, wherein the matrix bound with glycated protein comprises particles with a cross sectional length of about 0.01 to about 1,000 µm.

3. The device of claim 1, wherein the porous membrane is impermeable to the matrix bound with glycated protein.

4. A method of identifying glycated protein in a sample, the method comprising:
   (a) incubating a matrix to which a compound containing a boronic acid moiety is fixed with a sample including glycated protein and non-glycated protein in the first reaction chamber of the device for identifying glycated protein of claim 1 to provide a reaction mixture comprising a matrix bound with glycated protein;
   (b) removing the matrix bound with glycated protein from the reaction mixture by performing filtration through the separation unit of the device for identifying glycated protein of claim 1;
   (c) measuring a signal from the non-glycated protein in the reaction mixture; and
   (d) comparing the measured signal of the non-glycated protein in the reaction mixture with a signal measured from the sample including glycated protein and non-glycated protein, wherein the sample including glycated protein and non-glycated protein used for comparing the measured signal is obtained by incubating the matrix bound with glycated protein with a material having a higher affinity to boronic acid than glycated protein.

5. The method of claim 4, wherein the matrix to which a compound including a boronic acid moiety is fixed is a particle with a cross sectional length of about 10 nm to about 1,000 µm.

6. The method of claim 4, wherein the matrix to which a compound including a boronic acid moiety is fixed has a shape of a sphere, a polygon, a membrane, a plate, or a combination thereof.

7. The method of claim 6, wherein the membrane is a porous membrane.

8. The method of claim 4, wherein the glycated protein includes a glycated polypeptide or a glycated amino acid.

9. The method of claim 4, wherein the glycated protein is glycated hemoglobin, a fragment of glycated hemoglobin, a glycated amino acid, or a combination thereof.

10. The method of claim 4, wherein the measuring of the signal comprises measuring an optical signal, an electrical signal, a mechanical signal, or a combination thereof.

11. The method of claim 4, wherein the material having a higher affinity to the boronic acid than glycated protein includes sorbitol, mannitol, adonitol, erythritol, or a combination thereof.

* * * * *